United States Patent [19]
Park et al.

[11] Patent Number: 6,060,291
[45] Date of Patent: May 9, 2000

[54] FERMENTATION PROCESS FOR PREPARING ERYTHRITOL USING *TRICHOSPORONOIDES MADIDA* DS 911

[75] Inventors: Jin Byung Park, Anyang; Byung Cheol Seo, Seoul; Jung Ryul Kim, Yongin, all of Rep. of Korea

[73] Assignee: Doosan Corporation, Seoul, Rep. of Korea

[21] Appl. No.: 09/141,137

[22] Filed: Aug. 27, 1998

[30] Foreign Application Priority Data

Jun. 24, 1998 [KR] Rep. of Korea .................. 98-23831

[51] Int. Cl.⁷ .................................................. C12P 7/18
[52] U.S. Cl. ..................... 435/158; 435/254.1; 435/911
[58] Field of Search ............... 435/72, 105, 155, 435/158

[56] References Cited

U.S. PATENT DOCUMENTS 3,756,917  9/1973  Dezeeuw .
4,923,812  5/1990  Horikita .
5,902,739  5/1999  Abe et al. .................. 435/158
5,939,311  8/1999  Suh et al. .................. 435/254.11

OTHER PUBLICATIONS

Hajny, et al., *Applied Microbiology*, 12:3, pp. 240–246, May 1964.

Aoki, et al., *Biotechnology Letters*, 15:4, pp. 383–388, Apr. 1993.

*Primary Examiner*—Irene Marx
*Attorney, Agent, or Firm*—Kenyon & Kenyon

[57] ABSTRACT

The present invention relates to a fermentation process for preparing erythritol with high productivity using *Trichosporonoides madida* DS 911, more specifically, for preparing erythritol by optimizing the culture conditions such as pH, temperature, aeration rate and agitation speed, and by developing the process of fed-batch culture such as feeding strategy of substrate and composition of feeding substrate.

1 Claim, No Drawings

FERMENTATION PROCESS FOR PREPARING ERYTHRITOL USING *TRICHOSPORONOIDES MADIDA* DS 911

BACKGROUND OF THE INVENTION

1. Field of the Invention

The present invention relates to a fermentation process for preparing erythritol with high productivity using *Trichosporonoides madida* DS 911, more specifically, for preparing erythritol by optimizing the culture conditions such as pH, temperature, aeration rate and agitation speed, and by developing the process of fed-batch culture such as feeding strategy of substrate and composition of feeding substrate.

2. Description of Prior Art

Erythritol, a four carbon sugar alcohol, is a naturally occurring substance and is widely distributed in nature. Like most of the other polyols, it is a metabolite or storage compound for seaweeds and mushrooms. Fruits like melons, grapes and pears also contain erythritol. As it is often produced by bacteria, fungi, and yeasts, erythritol also occurs frequently in fermented food like wine, beer and soy sauce.

Erythritol is a moderately sweet bulking agent with 70~80 percent of the sweetness of sucrose in a 10 percent solution. Its high negative heat of solution provides the crystalline material with a strong cooling effect. As it has a taste which is very close to sucrose and with no bitter aftertaste, it is ideal to improve the taste in combination with intensive sweetener like aspartame.

Erythritol production from natural sources such as fruits and vegetables is not practical due to their relative small amounts. Erythritol can be chemically produced by reduction of meso-tartarate, oxidation and reduction of 4,6-o-ethylidene-D-glucose, hydrolysis of dealdehyde starch, or hydrogenation process. Since erythritol production by the chemical methods has been found to be expensive, it is worthwhile to explore an alternative method for the effective production of erythritol using microorganisms.

Erythritol can be biologically produced by microorganisms, especially genus of Candida (U.S. Pat. No. 3,756,917); genus of Aureobasidium (JP Pat. No. 2,626,692 and U.S. Pat. No. 4,923,812); genus of Trichosporonoides (Y. K. Park, *Biotechnology Letters* 15 (1993) pp 383–388) and genus of Moniliela (Hajiny, *Applied Microbiology* 12 (1964) pp 240–246).

However, the methods using such microorganisms have a few drawbacks in large scale production. More specifically, the method disclosed in U.S. Pat. No. 3,756,917 using the genus of Candida has low productivity due to its long cultivation period, even though the conversion ratio from n-paraffin is so high.

In the case of the genus of Aureobasidium, the method shows high fermentation yield of erythritol in the concentrated glucose medium compared to other microorganisms. However, the low production rate causes low productivity of erythritol in the case of batch mode fermentation (JP Pat. No. 2,626,692). Even though the productivity is highly increased in the case of cell-recycled continuous culture, there is no successful application in the large scale more than 50 m$^3$ in industry (U.S. Pat. No. 4,923,812).

On the other hand, the method using the genus of Trichosporonoides shows low productivity due to its long cultivation period even though the conversion ratio is comparatively high. Even though the method using the genus of Moniliela shows high conversion ratio in the high cencentrated glucose medium, the foam vigorously occures during the fermentation, which has to be removed using lots of xanthan gum.

SUMMARY OF THE INVENTION

The object of the present invention is to provide novel cell of *Trichosporonoides madida* DS 911, which was deposited to Korea Research Institute of Bioscience and Biotechnology, Korean Collection for Type Cultures (Address: KCTC, KRIBB #52, Oundong, Yusong-ku, Taejon 305–333, Republic of Korea), with accession number KCTC-0496BP on Jun. 18, 1998 under Budapest treaty, for preparing erythritol with high productivity.

The other object of the present invention is to provide the optimal culture conditions for maximum productivity of erythritol using *Trichosporonoides madida* DS 911 deposited to Korea Research Institute of Bioscience and Biotechnology with accession number KCTC-0496BP comprising the step of:

i) fermenting glucose medium with cells wherein
  a) composition of medium for maximum production of erythritol consists of 30~45 (w/v)% of glucose, 0.1~0.3 (w/v)% of yeast extract, 3~6 (w/v)% of corn steep liquor and 0.1~0.2 (w/v)% of phytic acid;
  b) pH of culture medium is 3~4;
  c) temperature of cultivation is 30~35° C.;
  d) aeration rate of the medium is 0.5~1.0 volume of air per volume of medium per minute; and
  e) agitation speed of the medium is 300~400 rpm;

ii) removing cells and other residue from the fermentation medium; and iii) separating and recovering erythritol from the fermentation medium of step (ii).

The further object of the present invention is to provide a fed batch fermentation process, wherein the glucose and corn steep liquor are fed together after the bleeding of culture broth from the fermentor, when the glucose was exhausted in the culture broth such as; wherein the fermentation is fed batch fermentation which characterizes i) feeding 10~40% culture broth when glucose is wholly depleted in culture broth;

ii) supplying the same volume of substrate, after feeding the culture broth; on condition that the composition of feeding substrate is glucose and corn steep liquor, and glucose concentration in culture broth is adjusted to 10~30%, and corn steep liquor to 0.05~2%.

DETAILED DESCRIPTION OF THE INVENTION

The present invention concerns a method for obtaining erythritol with a high yield and a high volumetric productivity using *Trichosporonoides madida* DS 911.

The novel cells used for the present invention are isolated by following method.

The material collected from honey comb is inoculated in a liquid medium consisting of 38~42% of glucose, 0.9~1.1% of yeast extract et al., suspended and cultivated for 5 days at 30° C. in a shaking incubator. The cultivated solution is spreaded in a plate medium consisting of 38~42% of glucose, 1.8~2.2% of yeast extract et al. and cultivated for 3 days at 30° C. The single colony is selected and cultivated in a medium consisting of 28~32% of glucose, 0.4~0.6% of yeast extract, 0.09~0.11% of urea et al. and cultivated for 5 days at 30° C. Then, *Trichosporonoides madida* DS 911 is isolated as the most erythritol producer compared to those of other cells by HPLC analysis.

This cell was named *Trichosporonoides madida* DS 911 and deposited to Korea Research Institute of Bioscience and Biotechnology with accession number KCTC-0496BP under Budapest Treaty.

The followings are biochemical properties of novel cell *Trichosporonoides madida* DS 911.

1. Morphological property

Colonies are usually restricted, and their surface is smooth or cerebriform, and initially cream colored, often finally olivaceous-brown in the PCA medium.

Budding cells often present, and their shapes are ellipsoidal, frequently composing a pseudomycelium in the PCA medium.

Hyphae is infrequently formed on malt agar with 40% additional saccharose, and it is hyaline, smooth and thin-walled, 2.5–3 µm wide, soon changing over into conidial chains.

Conidia is arising in terminal or lateral, unbranched or once branched, and acropetal chains from undifferentiated hyphae. Each chain is comprising up to 6 conidia, which are globose or ellipsoidal, and 6.5–15×3.5–7 µm on average, with inconspicous scars; terminal conidia is the shortest, and lower conidia is arthroconidium-like, and cylindrical with rounded ends.

2. Physiological properties

TABLE 1

| Fermentation property of sugar (*1) | |
| --- | --- |
| D-glucose | + |
| D-galactose | v |
| Sucrose | − |
| Maltose | − |
| Lactose | − |
| Raffinose | − |

(note) *1: The fermentation property was measured by the method of J. Lodder et al. using Wickerham preparation medium.
v: variable

TABLE 2

| Availability of sugar (*2) | |
| --- | --- |
| D-glucose | + |
| D-galactose | − |
| L-solbose | − |
| Sucrose | + |
| Maltose | v |
| Cellobiose | − |
| Trehalose | − |
| Lactose | − |
| Melibiose | − |
| Raffinose | − |
| Melezitose | − |
| Inulin | − |
| D-xylose | + |
| L-arabinose | + |
| D-arabinose | v |
| D-ribose | + |
| L-rhamnose | − |
| Glycerol | − |
| Erythritol | v |
| D-mannitol | v |
| α-methyl-D-glucoside | − |
| Salicin | − |
| Inositol | − |

(note) *2: The availability of sugar was measured by Biolog kit.
v: variable

TABLE 3

| Other properties | |
| --- | --- |
| Availability of nitrate | + |
| growth at 36° C. | + |
| necessity of vitamin | − |
| urea decomposition | + |
| DBB (*3) | + |

(note) *3: Diazonium Blue B

The microorganism of present invention has pseudohyphae, arthrospore and blastospore, and the shape of its colony is restricted and cerebriform. Therefore, the novel cell is classified as the species of *Trichosporonoides madida*. The inventors named this cell *Trichosporonoides madida* DS 911.

The followings are culture method using *Trichosporonoides madida* DS 911 for preparing erythritol with the maximum productivity.

Seed culture

The frozen (−70° C.) cells of *Trichosporonoides madida* DS 911 are cultivated in growth medium [30~50 (w/v)% of glucose, 0.9~1.1 (w/v)% of yeast extract and 1.9~2.1 (w/v)% of agar] at 32~38° C. for 3 days. And, the obtained cells are cultivated in growth medium [30~50 (w/v)% of glucose, 0.09~0.11 (w/v)% of yeast extract and 4~6 (w/v)% of corn steep liquor and 0.1~0.2 (w/v)% of phytic acid] at 32~38° C. for 2 days in a shaking incubator. This seed culture is transferred to a main fermentor for the erythritol production.

Main Culture

Experiments with fermentation medium are performed at 30~35° C. and 300~400 rpm in a 50L fermentor. The fermentation medium consists of 30~45 (w/v)% of glucose, 0.1~0.5 (w/v)% of yeast extract, 3~6 (w/v)% of corn steep liquor and 0.1~0.2 (w/v)% of phytic acid as carbon source and nitrogen sources. Aeration rate is in the range of 0.5~1.0 vvm.

The fermentation process is preferably by fed-batch process. When the glucose is completely consumed in the medium, the concentration of erythritol is measured by high performance liquid chromatography equipped with carbohydrate analysis column (YMC pack polyamine II, Japan).

The conversion yield of erythritol is 40~50% and volumetric productivity is 1.5~2.0 g/L-hr in fed-batch cultures, which correspond to 5~15% increase compared with simple batch fermentation. The culture time includes the time that used for the prepartion of culture medium.

Finally the fermentation medium is centrifuged for removing cells and other residues, and the supernatant is filtered and purified for obtaining erythritol crystal.

The present invention can be explained more specifically by following examples.

EXAMPLE 1

The frozen (−70° C.) cells of *Trichosporonoides madida* DS 911 are cultivated in the medium [40 (w/v)% of glucose, 1.0 (w/v)% of yeast extract and 2.0 (w/v)% of agar] at 35° C. for 3 days. Thereafter, the obtained cells are cultivated in growth medium [30 (w/v)% of glucose, 0.1 (w/v)% of yeast extract, 5 (w/v)% of corn steep liquor and 0.1 (w/v)% of phytic acid] at 35° C. for 2 days in a shaking incubator. This seed culture broth is transferred to a main fermentor for the production of erythritol.

Experiments with fermentation medium are performed at 35° C. and 300 rpm, 1.0 vvm for 3 days in a 50L fermentor.

The fermentation medium consists of 30 (w/v)% of glucose, 0.1 (w/v)% of yeast extract, 4 (w/v)% of corn steep liquor and 0.1 (w/v)% of phytic acid as carbon source and nitrogen sources.

After 72 hours fermentation, the final concentration of erythritol is 14.1% and a small amount of glycerol is obtained. Finally the fermentation medium is centrifuged for removing cells and other residues, and the supernatant is filtered and purified by active carbon and ion exchange resin for obtaining the crystal of erythritol. The melting point of obtained crystal is 122° C. and by HPLC and NMR analysis, it is identified as meso-erythritol.

EXAMPLE 2

Experiments with fermentation medium are performed at 35° C. and 200 rpm for 5~8 days in a shaking incubaor. The fermentation medium consists of 30~45 (w/v)% of glucose, 0.1 (w/v)% of yeast extract, 4 (w/v)% of corn steep liquor and 0.1 (w/v)% of phytic acid as carbon source and nitrogen sources. Table 4 shows the results of the fermentation.

TABLE 4

| Concentration of glucose (%) | Fermentation period (day) | Erythritol (g/L) | Glycerol (g/L) | Yield (%) |
| --- | --- | --- | --- | --- |
| 30 | 5 | 141 | 2 | 47 |
| 35 | 6 | 165 | 6 | 47 |
| 40 | 7 | 184 | 14 | 46 |
| 45 | 8 | 189 | 25 | 42 |

EXAMPLE 3

Experiments with fermentation medium are performed at 35° C. and 200 rpm for 5 days in a shaking incubator. The fermentation medium consists of 40 (w/v)% of glucose, 0.1 (w/v)% of yeast extract, 4 (w/v)% of corn steep liquor and 0.1 (w/v)% of phytic acid as carbon source and nitrogen sources. The pH is adjusted to 3.5~5.0. Table 5 shows the results of the fermentation.

TABLE 5

| pH | Erythritol (g/L) | Glycerol (g/L) | Yield (%) |
| --- | --- | --- | --- |
| 3.0 | 136 | 5 | 45 |
| 3.5 | 141 | 2 | 47 |
| 4.0 | 142 | 3 | 47 |
| 5.0 | 140 | 3 | 47 |

EXAMPLE 4

Experiment with fermentation medium is performed at 35° C. and 300 rpm, 1.0 vvm for 84 hours in a 50L fermentor. The fermentation medium consists of 40 (w/v)% of glucose, 0.1 (w/v)% of yeast extract, 4 (w/v)% of corn steep liquor and 0.1 (w/v)% of phytic acid. The pH is adjusted to 3.5. After 84 hours of fermentation, the final concentration of erythritol is 18.9% and the productivity of erythritol is 2.25 g/L-h which corresponds to more than 10% higher productivity compared with that in the genus of Aureobasidium (JP Pat. No. 2,626,692).

EXAMPLE 5

Experiments with fermentation medium are performed at 35° C. and 300 rpm, 1.0 vvm in a 50L fermentor. The fermentation medium consists of 40 (w/v)% of glucose, 0.1 (w/v)% of yeast extract, 4 (w/v)% of corn steep liquor and 0.1 (w/v)% of phytic acid as carbon source and nitrogen sources. The pH is adjusted to 3.5. When the glucose was used up, 5L of culture broth is bleeded and the same volume of glucose syrup (720 g/L) and 175 g of corn steep liquor are inserted to the fermentor. After 21 hours of fermentation, glucose is exhausted. The final concentration of erythritol is 21.1% and the erythritol concentration of bleeded culture broth is 18.7%. The productivity of erythritol is 1.84 g/L-h.

EXAMPLE 6

Experiments with fermentation medium are performed at 35° C. and 300 rpm, 1.0 vvm in a 50L fermentor. The fermentation medium consists of 40 (w/v)% of glucose, 0.1 (w/v)% of yeast extract, 4 (w/v)% of corn steep liquor and 0.1 (w/v)% of phytic acid as carbon source and nitrogen sources. The pH is adjusted to 3.5. When the glucose is used up, 10L of culture broth is bleeded and the same volume of glucose syrup and 350 g of corn steep liquor are fed into the fermentor. After 42 hours of fermentation, glucose is completely exhausted. The final concentration of erythritol is 23.3% and the erythritol concentration of bleeded culture broth is 18.5%. Volumetric productivity is 1.91 g/L-hr which correspond to 10% increase compared with the simple batch fermentation (Example 4).

We claim:

1. A fermentation process for maximum production of erythritol using *Trichosporonoides madida* DS 911 accession number KCTC-0496BP comprising the steps of:

i) fermenting said *Trichosporonoides madida* in a glucose fermentation medium comprising
  a) from 30–45 (w/v)% of glucose, from 0.1–0.3 (w/v)% of yeast extract, from 3–6 (w/v)% of corn steep liquor and from 0.1–0.2 (w/v) of phytic acid;
  b) pH of culture medium is 3–4;
  c) temperature of cultivation is 30–35° C.;
  d) aeration rate of medium is 0.5–1.0 volume of air per volume of medium per minute; and
  e) agitation speed of the medium is 300–400 rpm;
 ii) removing cells and other residue from the fermentation medium; and
 iii) separating and recovering erythritol from the fermentation medium of step (ii).

* * * * *